US012614287B2

(12) United States Patent
Fathollahi Ghezelghieh et al.

(10) Patent No.: US 12,614,287 B2
(45) Date of Patent: Apr. 28, 2026

(54) TRACKING MULTIPLE SURGICAL TOOLS IN A SURGICAL VIDEO

(71) Applicant: Verb Surgical Inc., Santa Clara, CA (US)

(72) Inventors: Mona Fathollahi Ghezelghieh, Sunnyvale, CA (US); Jocelyn Barker, San Jose, CA (US)

(73) Assignee: Auris Health, Inc., Santa Clara, CA (US)

( * ) Notice: Subject to any disclaimer, the term of this patent is extended or adjusted under 35 U.S.C. 154(b) by 489 days.

(21) Appl. No.: 18/077,912

(22) Filed: Dec. 8, 2022

(65) Prior Publication Data

US 2023/0177703 A1     Jun. 8, 2023

Related U.S. Application Data

(60) Provisional application No. 63/287,477, filed on Dec. 8, 2021.

(51) Int. Cl.
| | |
|---|---|
| *G06T 7/246* | (2017.01) |
| *A61B 34/20* | (2016.01) |
(Continued)

(52) U.S. Cl.
CPC .............. *G06T 7/246* (2017.01); *A61B 34/20* (2016.02); *G06V 10/26* (2022.01); *G06V 10/761* (2022.01);
(Continued)

(58) Field of Classification Search
CPC ............ A61B 34/20; A61B 2034/2055; A61B 2034/2057; A61B 2034/2065
See application file for complete search history.

(56) References Cited

U.S. PATENT DOCUMENTS

| | | | |
|---|---|---|---|
| 2015/0297313 | A1 | 10/2015 | Reiter et al. |
| 2021/0290317 | A1 | 9/2021 | Sen et al. |

FOREIGN PATENT DOCUMENTS

| | | |
|---|---|---|
| CN | 112037263 A | 12/2020 |

OTHER PUBLICATIONS

Fujie, Hiroki, et al. "Detecting and Tracking Surgical Tools for Recognizing Phases of the Awake Brain Tumor Removal Surgery." ICPRAM. 2019. (Year: 2019).*

(Continued)

*Primary Examiner* — Raphael Schwartz
(74) *Attorney, Agent, or Firm* — Aikin & Gallant, LLP

(57) ABSTRACT

Disclosed are various systems and techniques for tracking surgical tools in a surgical video. In one aspect, the system begins by receiving one or more established tracks for one or more previously-detected surgical tools in the surgical video. The system then processes a current frame of the surgical video to detect one or more objects using a first deep-learning model. Next, for each detected object in the one or more detected objects, the system further performs the flowing steps to assign the detected object to a right track: (1) computing a semantic similarity between the detected object and each of the one or more established tracks; (2) computing a spatial similarity between the detected object and the latest predicted location for each of the one or more established tracks; and (3) attempting to assign the detected object to one of the one or more established tracks based on the computed semantic similarity and the spatial similarity metric.

20 Claims, 6 Drawing Sheets

(51) Int. Cl.

| | |
|---|---|
| *G06V 10/26* | (2022.01) |
| *G06V 10/74* | (2022.01) |
| *G06V 10/764* | (2022.01) |
| *G06V 10/77* | (2022.01) |
| *G06V 10/774* | (2022.01) |
| *G06V 10/82* | (2022.01) |

(52) U.S. Cl.
CPC ........ *G06V 10/764* (2022.01); *G06V 10/7715* (2022.01); *G06V 10/774* (2022.01); *G06V 10/82* (2022.01); *A61B 2034/2065* (2016.02); *G06T 2207/10016* (2013.01); *G06T 2207/10068* (2013.01); *G06V 2201/034* (2022.01)

(56) References Cited

OTHER PUBLICATIONS

Robu, Maria, et al. "Towards real-time multiple surgical tool tracking." Computer Methods in Biomechanics and Biomedical Engineering: Imaging & Visualization 9.3 (Dec. 3, 2020): 279-285. (Year: 2020).*

Liu, Liqiang, and Jianzhong Cao. "End-to-end learning interpolation for object tracking in low frame-rate video." IET Image Processing 14.6 (Apr. 2020): 1066-1072. (Year: 2020).*

Bewley, Simple Online and Realtime Tracking, 2017, https://arxiv.org/abs/1602.00763v2 (Year: 2017).*

Bergmann, P., "Tracking without bells and whistles", Proceedings of the IEEE/CVF International Conference on Computer Vision (ICCV), 2019, pp. 941-951.

Harmans, A., et al., "In Defense of the Triplet Loss for Person Re-Identification", arXiv:1703.07737v4 [cs.CV], Nov. 21, 2017, 17 pages.

Lee, D., et al., "Evaluation of Surgical Skills during Robotic Surgery by Deep Learning-Based Multiple Surgical Instrument Tracking in Training and Actual Operations", Journal of Clinical Medicine, vol. 9, No. 6, 15 pages.

Robu, M., et al., "Towards real-time multiple surgical tool tracking", Computer Methods in Biomechanics and Biomedical Engineering: Imaging & Visualization>, vol. 9, No. 3, 12 Pages.

PCT/IB2022/061944, "PCT Notification of Transmittal of the International Search Report and the Written Opinion of the International Searching Authority, or the Declaration", Mailed Mar. 15, 2023, 7 pages.

Supplementary European Search Report received for European Patent Application No. 22903708.0, mailed Oct. 22, 2025, 11 pages.

Anonymous: "Hungarian Algorithm;" WIKIPEDIA, The Free Encyclopedia; retrieved online: https://simple.wikipedia.org/wiki/Hungarian_algorithm; Nov. 15, 2021; 15 pages.

Fathollahi et al.; "Video-based Surgical Skills Assessment using Long term Tool Tracking;" retrieved online: https://doi.org/10.48550/arXiv.2207.02247; Jul. 5, 2022; 11 pages.

Wojke et al.; "Simple Online and Realtime Tracking with a Deep Association Metric;" retrieved online: https://doi.org/10.48550/arXiv.1703.07402v1; Mar. 21, 2017; 5 pages.

* cited by examiner

MULTIPLE SURGICAL TOOL TRACKING (MSTT) SYSTEM 100

RAW VIDEO FRAMES 120

VIDEO PRE-PROCESSING MODULE 102

PREPROCESSED VIDEO FRAMES 122

TOOL DETECTION MODULE 104

DETECTION MODEL 114

DETECTED OBJECTS 124

TOOL TRACKING MODULE 106

RE-ID MODEL 116

UNASSIGNED DETECTIONS 126

TOOL RE-IDENTIFICATION MODULE 108

RECOVERED TRACKS 128

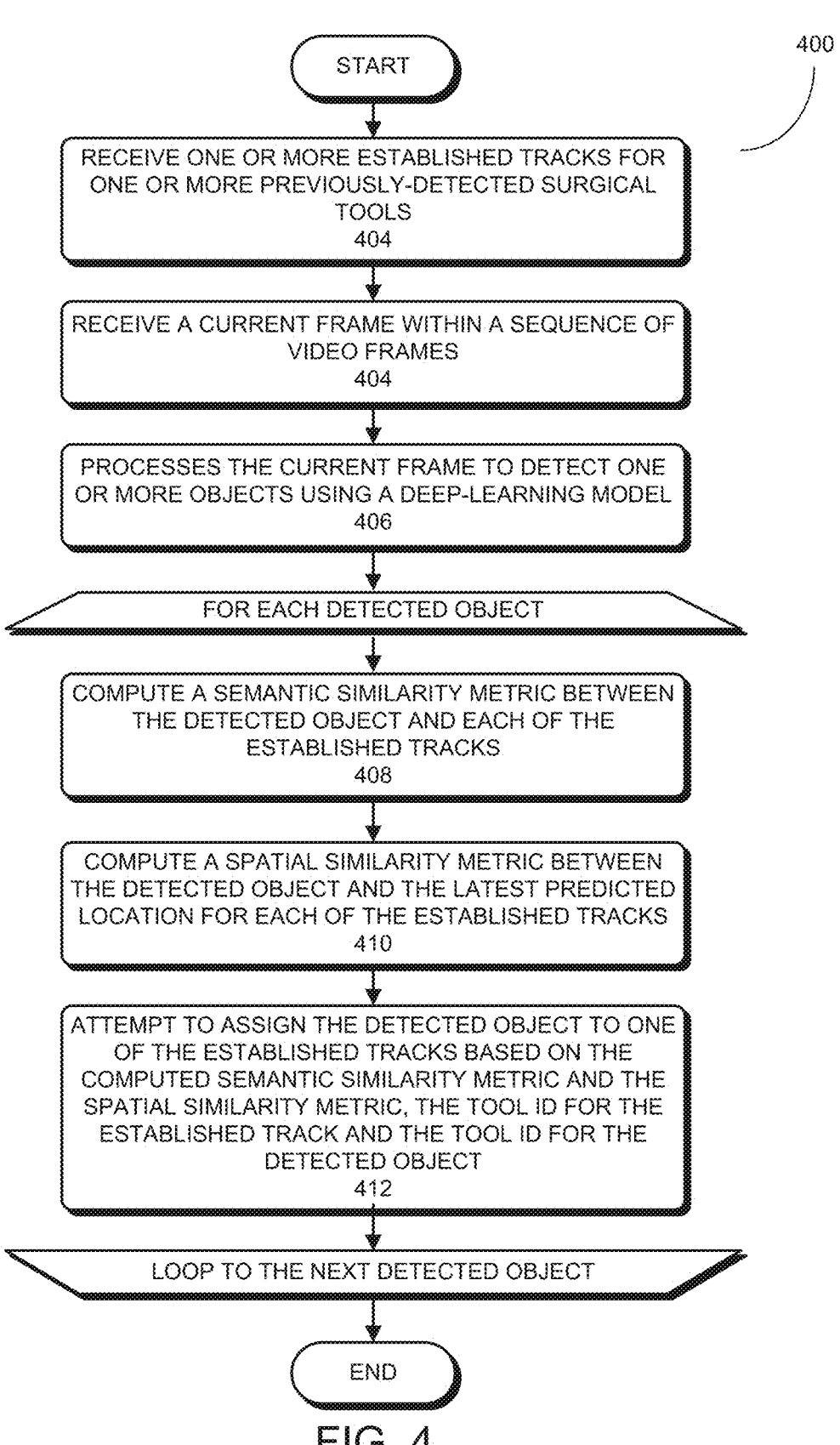

400

START

RECEIVE ONE OR MORE ESTABLISHED TRACKS FOR
ONE OR MORE PREVIOUSLY-DETECTED SURGICAL
TOOLS
404

RECEIVE A CURRENT FRAME WITHIN A SEQUENCE OF
VIDEO FRAMES
404

PROCESSES THE CURRENT FRAME TO DETECT ONE
OR MORE OBJECTS USING A DEEP-LEARNING MODEL
406

FOR EACH DETECTED OBJECT

COMPUTE A SEMANTIC SIMILARITY METRIC BETWEEN
THE DETECTED OBJECT AND EACH OF THE
ESTABLISHED TRACKS
408

COMPUTE A SPATIAL SIMILARITY METRIC BETWEEN
THE DETECTED OBJECT AND THE LATEST PREDICTED
LOCATION FOR EACH OF THE ESTABLISHED TRACKS
410

ATTEMPT TO ASSIGN THE DETECTED OBJECT TO ONE
OF THE ESTABLISHED TRACKS BASED ON THE
COMPUTED SEMANTIC SIMILARITY METRIC AND THE
SPATIAL SIMILARITY METRIC, THE TOOL ID FOR THE
ESTABLISHED TRACK AND THE TOOL ID FOR THE
DETECTED OBJECT
412

LOOP TO THE NEXT DETECTED OBJECT

END

FIG. 4

TRACKING MULTIPLE SURGICAL TOOLS IN A SURGICAL VIDEO

PRIORITY CLAIM AND RELATED PATENT APPLICATIONS

This patent application claims the benefit of U.S. Provisional Patent Application Ser. No. 63/287,477, entitled "MOTION TRACKING OF SURGICAL INSTRUMENT," filed on 8 Dec. 2021, the contents of which are incorporated by reference herein.

TECHNICAL FIELD

This invention generally relates to surgical tool motion tracking, and more specifically to systems and methods for tracking multiple surgical tools using machine learning and analyzing the tracked motions.

BACKGROUND

Tracking a surgeon's instrument movements during minimally invasive surgery (MIS) is a critical step towards providing actionable feedback to the surgeon, issuing real-time guidance, and automating procedure steps. Tool-motion metrics calculated from the instrument movement paths have been shown to correlate with surgeon experience, learning curve progression, and patient outcome measures. Typically, it is only feasible to calculate tool-motion metrics for robot-assisted MIS procedures, and with access to the robot data via a research partnership with the surgical robot vendor.

Tracking surgical tools in an endoscope video feed is a challenging problem because the appearance of the same tool can vary significantly through a video sequence. For example, during a video sequence, the jaw of a surgical tool can be first open then closed, a portion of the tool may be occluded by tissue, and the surgeon may move the tool too fast that leads to motion blur. Moreover, simultaneously tracking a left-hand tool and a right-hand tool presents additional challenges because sometimes the left-hand and right-hand tools can become very similar to each other in appearances, making it difficult to distinguish between the left and right tools in these frames. Furthermore, tracking surgical tools through a long video segment or a long surgical step is extremely challenging because each tool can leave the camera view once or multiple times during such long surgical step/video segment.

Hence, what is needed is a system and a technique for reliably tracking more than one surgical tools through a segment of a surgical video and assigning a newly detected tool to a right track without the deficiencies of the existing techniques.

SUMMARY

Disclosed are various video-based tool motion tracking systems and techniques based on computer vision and deep learning. More specifically, the disclosed tool motion tracking systems and techniques employ various computer vision and deep learning models configured to both detect new tools entering video frames and continuously generate tool positional data that can be used to calculate motion trajectories and other motion metrics based exclusively on laparoscope video feeds. Because the disclosed tool motion tracking systems and techniques can simultaneously track multiple surgical, the disclosed tool motion tracking systems and techniques are also referred as "multiple surgical tool tracking" (MSTT) systems and techniques.

Specifically, the disclosed MSTT systems and techniques employ at least two deep-learning models: a first model configured for detecting one or more surgical tools within each video frame, and a second model configured to simultaneously track multiple surgical tools by estimating the trajectories of several tools simultaneously present within a video segment and assigning the newly detected objects to the right trajectories. Note that the two deep-learning models operate in tandem in a tracking-by-detection framework, which is designed to link detected objects across a sequence of frames correctly based on the localized bounding boxes of the detected objects. Moreover, the second model is also configured to re-identify tools after they have temporally left the video frames and the corresponding tracks become inactive. Using the disclosed tool tracking model, the MSTT systems and techniques can estimate the trajectory for each of the tracked tools by establishing the (x, y) coordinates continuously for the tracked tool, e.g., for both the left-hand and right-hand tools that a surgeon uses throughout a given surgical step or task. In some embodiments, after generating the trajectories by the disclosed MSTT systems and techniques, the surgeon performance metrics such as path length and derivatives of displacement can be calculated based on these trajectories.

The MSTT systems and techniques are able to estimate the trajectory (i.e., the x and y image locations) of right and left tools that the surgeon uses in each surgical task. The proposed multi-tool tracking framework employs a tracking-by-detection scheme wherein at each new frame, active-used tools are detected and assigned to the existing tracks. The MSTT systems and techniques require two deep-learning models that is trained in advanced: the first one is a "tool detection" model, based on Faster-RCNN model, trained to localize surgical tools at each frame of the video; and the second model is a re-identification (or "re-ID") model that is trained to distinguish between multiple simultaneously detected tools. The re-ID model is trained to learn feature descriptions of each generated bounding box of a detected tool such that if two bounding boxes belong to the same track, then their feature corresponding descriptors should be close in Euclidean space compared to two feature descriptors of bounding boxes corresponding to two different tracks.

In one aspect, a process for tracking surgical tools in a surgical video is disclosed. The process begins by receiving one or more established tracks for one or more previously-detected surgical tools in the surgical video. The process then processes a current frame of the surgical video to detect one or more objects using a first deep-learning model. Next, for each detected object in the one or more detected objects, the process further performs the flowing steps to assign the detected object to a right track: (1) computing a semantic similarity between the detected object and each of the one or more established tracks; (2) computing a spatial similarity between the detected object and the latest predicted location for each of the one or more established tracks; and (3) attempting to assign the detected object to one of the one or more established tracks based on the computed semantic similarity and the spatial similarity metric.

In some embodiments, prior to processing the current frame, the process converts a frame rate of the surgical video so that the converted frame rate is greater or equal to a predetermined frame rate, and resizes the current frame into a predetermined image size.

3

In some embodiments, the first deep-learning model is a Faster-RCNN model trained to detect and classify a set of diverse types of surgical tools within a given video frame of the surgical video.

In some embodiments, the one or more previously-detected surgical tools include a left-hand tool and a right-hand tool.

In some embodiments, the process computes the spatial similarity between the detected object and the latest predicted location for each of the one or more established tracks by: (1) using a second deep-learning model to extract a set of image features from the detected object; and (2) comparing the set of extracted image features with multiple sets of stored image features associated with the established track to determine whether the detected object and the previously-detected images of the surgical tool associated with the established track are visually similar.

In some embodiments, the set of image features forms a feature vector of 128 dimensions.

In some embodiments, the multiple sets of stored image features are associated with a number of previously-detected images of the surgical tool over a predetermined time period.

In some embodiments, prior to computing the spatial similarity, the process receives a location on the generated bounding box for the detected object. The process then generates the latest predicted location for the established track by applying a Kalman filter to the received location of the detected object and the last known location of the established track.

In some embodiments, location of the bounding box is the center of the bounding box.

In some embodiments, the process attempts to assign the detected object to one of the established tracks by using a data association technique on the computed semantic similarity and the computed spatial similarity metrics between the detected object and each of the one or more established tracks.

In some embodiments, the data association technique employs a Hungarian method that is configured to identify a correct track assignment within the one or more established tracks for the detected object by minimizing a cost function of the track assignment between the detected object and the one or more established tracks.

In some embodiments, the Hungarian method employs a bipartite graph to solve the cost function associated with the detected object.

In some embodiments, the process assigns a very high weight to a track assignment if the corresponding computed spatial similarity is greater than a predetermined distance threshold to prohibit the said track assignment.

In some embodiments, the cost function additionally includes a track ID associated with the established track and a class ID assigned to the detected object.

In some embodiments, the process assigns a very high weight to a track assignment if the corresponding track ID associated with the established track does not match the class ID of the detected object to prohibit the said track assignment.

In some embodiments, the process further includes the steps for recovering an inactive track by: (1) receiving a detected object in the one or more detected objects that cannot be assigned to any track in the one or more established tracks; and (2) determining if the location of the unassigned object is sufficiently close to the last known location of an inactive track in the one or more established tracks and if a class ID of the unassigned object matches a track ID of the inactive track; and (3) if so, re-assigning the unassigned object to the inactive track to reactivate the previously established track that has become inactive.

BRIEF DESCRIPTION OF THE DRAWINGS

The structure and operation of the present disclosure will be understood from a review of the following detailed description and the accompanying drawings in which like reference numerals refer to like parts and in which:

FIG. 4 presents a flowchart illustrating an exemplary process for tracking one or more surgical tools through a sequence of video frames of a surgical video in accordance with some embodiments described herein.

DETAILED DESCRIPTION

Figure 1:
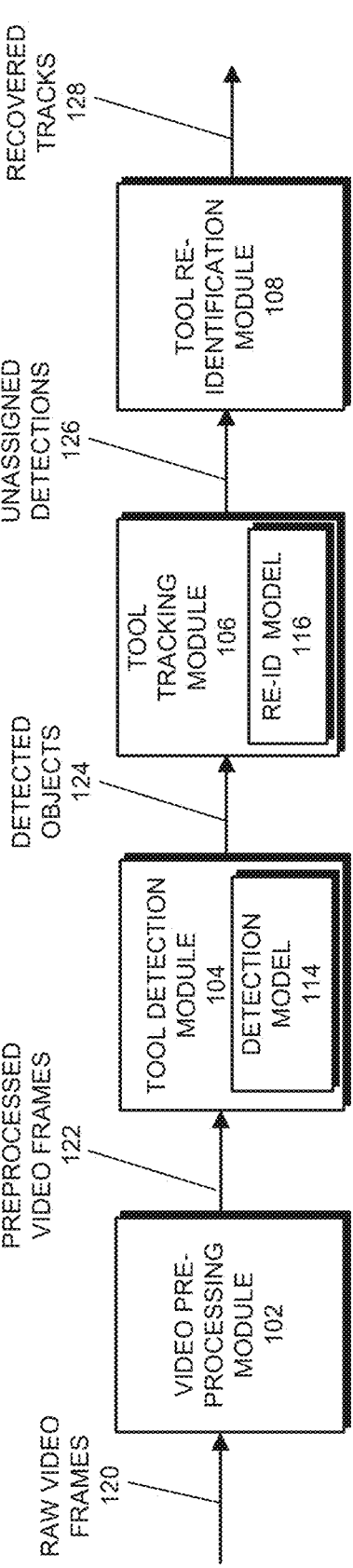
FIG. 1 shows a diagram illustrating an exemplary multiple surgical tool tracking (MSTT) system for implementing the disclosed user-presence/absence recognition techniques in accordance with some embodiments described herein.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced without these specific details. In some instances, structures and components are shown in block diagram form in order to avoid obscuring the concepts of the subject technology.

Disclosed are various video-based tool motion tracking systems and techniques based on computer vision and deep learning. More specifically, the disclosed tool motion tracking systems and techniques employ various computer vision and deep learning models configured to both detect new tools entering video frames and continuously generate tool positional data that can be used to calculate motion trajectories and other motion metrics based exclusively on laparoscope video feeds. Because the disclosed tool motion tracking systems and techniques can simultaneously track multiple surgical, the disclosed tool motion tracking systems and techniques are also referred as "multiple surgical tool tracking" (MSTT) systems and techniques.

Specifically, the disclosed MSTT systems and techniques employ at least two deep-learning models: a first model configured for detecting one or more surgical tools within each video frame, and a second model configured to simultaneously track multiple surgical tools by estimating the trajectories of several tools simultaneously present within a video segment and assigning the newly detected objects to the right trajectories. Note that the two deep-learning models operate in tandem in a tracking-by-detection framework, which is designed to link detected objects across a sequence of frames correctly based on the localized bounding boxes of the detected objects. Moreover, the second model is also configured to re-identify tools after they have temporally left the video frames and the corresponding tracks become inactive. Using the disclosed tool tracking model, the MSTT systems and techniques can estimate the trajectory for each of the tracked tools by establishing the (x, y) coordinates continuously for the tracked tool, e.g., for both the left-hand and right-hand tools that a surgeon uses throughout a given surgical step or task. In some embodiments, after generating the trajectories by the disclosed MSTT systems and techniques, the surgeon performance metrics such as path length and derivatives of displacement can be calculated based on these trajectories.

The MSTT systems and techniques are able to estimate the trajectory (i.e., the x and y image locations) of right and left tools that the surgeon uses in each surgical task. The proposed multi-tool tracking framework employs a tracking-by-detection scheme wherein at each new frame, active-used tools are detected and assigned to the existing tracks. The MSTT systems and techniques require two deep-learning models that is trained in advanced: the first one is a "tool detection" model, based on Faster-RCNN model, trained to localize surgical tools at each frame of the video; and the second model is a re-identification (or "re-ID") model that is trained to distinguish between multiple simultaneously detected tools. The re-ID model is trained to learn feature descriptions of each generated bounding box of a detected tool such that if two bounding boxes belong to the same track, then their feature corresponding descriptors should be close in Euclidean space compared to two feature descriptors of bounding boxes corresponding to two different tracks. The disclosed MSTT systems and techniques allow for tracking more than one surgical tool in a video feed for an extended duration, e.g., from a few minutes to 10s of minutes.

FIG. 1 shows a diagram illustrating an exemplary multiple surgical tool tracking (MSTT) system 100 for implementing the disclosed user-presence/absence recognition techniques in accordance with some embodiments described herein. As shown in FIG. 1, robotic surgical system 100 can include at least the following functional modules: a video preprocessing module 102, a tool detection module 104, a tool tracking module 106, and a tool re-identification module 108, which are coupled with each other in the order shown. In particular, tool detection module 104 further includes a deep-learning-based tool detection model 114 which has been trained to perform surgical tool localization on video images. Moreover, tool re-identification module 110 includes a deep-learning-based tool re-identification model 120 which has been trained to re-identify a surgical tool in a received video frame that has temporarily disappeared from the video frames.

During operation, the disclosed MSTT system 100 can begin when a video preprocessing module 102 receives a sequence of raw video frames 120. In some embodiments, video preprocessing module 102 includes a function or a submodule to increase the received raw video frames 120 to a frame rate at least equal to a predetermined frame rate, e.g., at 30 frame-per-second (30 fps). In other words, if the incoming frame rate of the raw video frames 120 is below the predetermined frame rate (e.g., incoming frame rate=15 fps), video preprocessing module 102 up-converts the video 120 to at least the predetermined frame rate (e.g., to 30 FPS). For example, video preprocessing module 102 can use one of linear interpolation and optic flow technique to perform this upconversion. Furthermore, video preprocessing module 102 may also include a function or a submodule to resize each higher resolution image of the received raw video frames 120 to a quarter high definition at 960×540. Note that the two functions or submodules for frame rate conversion and image resizing can be performed sequentially in any given order. Moreover, one or both of these two functions or submodules may be omitted. When both of these functions or submodules are omitted, video preprocessing module 102 may be omitted from MSTT system 100. Otherwise, video preprocessing module 102 outputs preprocessed video frames 122.

For each video frame in the received preprocessed video frames 122, tool detection module 104 is configured to apply deep-learning tool detection model 114 on the video frame, and generate one or more detected objects 124 (in the form of localized and classified bounding boxes) as outputs. In some embodiments, deep-learning tool detection model 114 is implemented based on a Faster-RCNN (regions convolutional neural network) architecture. Specifically, such a Faster-RCNN-based detection model has been trained to localize each surgical tool within each frame of the video, such as in each preprocessed video frame 122. In some embodiments, localizing a given surgical tool within the video frame includes generating a bounding box around the end effector portion of the detected surgical tool.

In some embodiments, the tool detection model 114 was trained on a training dataset constructed to include various scenarios of tool configurations/appearances of a given surgical tool, such as a pair of grasper, during a surgical procedure. Note that a given surgical tool can take on different configurations/appearances during a surgery procedure. For example, the jaws of a given tool may be in an open state (which can further vary in terms of a degree of being open) or in a closed state. Moreover, a given tool can vary in perspectives in different frames (e.g., in different spatial angles, or in different distances to the camera lens). Furthermore, a given tool can also appear partially occluded, e.g., by anther tool or by a tissue. To be able to detect the same surgical tool in such a wide variety of possible scenarios when the surgical tool is in use, the train dataset should also include a diverse set of sample images that cover all of the practical scenarios of the surgical configurations/appearances.

In some embodiments, a set of training surgical videos is collected from gastric bypass and sleeve gastrectomy procedures. Next, images of surgical tools captured in each training video are cropped out and labeled by one or more human annotators to provide the ground truth labels to the surgical tool images. Note that the constructed training dataset includes multiple subsets of labeled training images for multiple surgical tools, wherein each subset of labeled training images is specifically constructed for a unique surgical tool in a wide variety of configurations/appearances. After constructing such a multi-tool detected training dataset, the training dataset is split into a training set (e.g., 80% of the total training dataset) and a validation set (e.g., 20% of the total training dataset). When tool detection model 114 has been trained and validated on such a training dataset, the trained tool detection model 114 can be applied to a real-time video feed to detect multiple surgical tools, and for each of the surgical tool, a wide variety of configurations/appearances of the tool. During deployment, the trained tool detection model 114 continues to generate localized bounding boxes for a given tool, wherein the location and size (in terms of width and height) of the generated bounding boxes can continue to change. In some embodiments, detection model 114 is configured such that each tool detection is validated only when the confidence score associated with the detection is above a predetermined threshold.

After a new tool is detected by tool detection module 104 within a newly processed frame 122, tool tracking module 106 in MSTT system 100 is configured to begin tracking the newly-detected tool through subsequently video frames 122 based on the corresponding localized bounding boxes and the associated tool ID continue to be generated by tool detection module 104. Note that tool tracking module 106 includes a deep-learning-based re-ID model 116 configured to process a cropped image within a generated bounding box of a detected tool to determine whether the detected tool belongs to one of the established tracks. In some embodiments, re-ID model 116 has been trained to generate a feature vector of a predetermined dimension, e.g., 128 for the input image to represent the detected tool in the cropped image. The newly generated feature vector can then be compared to previously generated feature vectors of identified tools to determine if the detected tool belongs to one of the previously identified tools. The detailed operations of the re-ID model 116 will be described below. In some embodiments, to allow the newly-detected tool to be tracked, tool tracking module 106 can explicitly generate a tracking request for the newly-detected tool. However, tool tracking module 106 can also be configured to automatically trigger a new tracking process in response to detecting a tool in a frame that has not been previously detected (i.e., the assigned tool ID has not been assigned before).

In some embodiments, each new tracking process begins with initiating a track for each unique detection from an initial video frame or multiple initial frames. Specifically, tool tracking module 106 can initiate a track with a unique track ID, which can be identical to a unique tool ID generated by tool detection module 104. Note that for multi-tool tracking, the multiple tools may or may be initially detected in the same initial frame. However, if tool detection module 104 detects multiple unique tools from a single initial frame, tool tracking module 106 is configured to simultaneously initiate multiple tracks corresponding to the multiple unique tool detections (e.g., both the left tool and the right tool). Alternatively, if tool detection module 104 sequentially generates two or more unique tool detections from a number of initial frames, tool tracking module 106 is configured to sequentially initiate two or more tracks corresponding to the two or more sequential detections.

Note that a common scenario of multiple tools in a video segment is when a surgeon simultaneously holds a first tool in the left hand (or simply "left-hand tool" or "left tool") and a second tool in the right hand (or simply "right-hand tool" or "right tool") and operates the left tool and the right tool with both hands. In some embodiments, to initiate two tracks for the left tool and the right tool, the initial designations of the left or the right tool after both tools are detected in a processed video frame 122 can be directly decided by a user through a manual entry. In other words, a user will review the new detections and specify with an input means which detection is for the left tool and which one is for the right tool. Subsequently, two tracklets (or simply "tracks" below) are initialized for the left and right tools based on the received manual entries from the user. However in other embodiments, tool tracking module 106 may be configured to automatically determine and designation the left tool and which one is for the right tool, e.g., based on the relative positions of the detections. For example, tool tracking module 106 can automatically designate the detected tool appearing on the left side of the video frame as the left tool, and the detected tool appearing on the right side of the video frame as the right tool. Subsequently, tool detection module 104 is configured to simultaneously track the left tool and right tool by constructing two independent tracks. Note that by correctly initiating the left tool and right tool at the beginning, tool detection module 104 can then separately track the left tool and the right tool in the subsequent frames, even if the two tools are the same type of tools (e.g., both are graspers).

In various embodiments, a tool tracking process can begin when at least one track has been initialized or instantiated. However, when more than one track has been initialized (e.g., when both the left-tool track and the right-tool track have been initialized), the tool tracking process becomes a multi-tool tracking process. During a multi-tool tracking process, tool detection module 104 continues to operate as usual, i.e., to process each newly received video frame 122 and generate localized bounding boxes for the detected tools in the new frame. Subsequently, for each newly-detected object (also referred to as a "new detection") in the new frame, tool tracking module 106 is configured to determine whether the newly-detected object belongs to one of the existing/established tracks. If so, the new detection is assigned to one of the established tracks. For example, after the left-tool track and the right-tool track have been established, and when tool detection module 104 generates two localized bounding boxes for two detected tools in a newly received video frame, tool tracking module 106 is configured to assign each of the two new detections to a corresponding left-tool track or the right-tool track. Note that after the assignments of the new detections to the established tracks, the locations of the new detections can be used to update the most-recent locations of the established tracks.

In various embodiments, tool tracking module 106 is configured to assign a new detection to a corresponding established track by evaluating a set of metrics. The set of metrics can include: (1) a semantic similarity metric: (2) a spatial similarity metric; and (3) a class-ID matching metric. Specifically, the semantic similarity compares images feature similarities between a newly-detected object and stored tool images associated with an existing tracking. The spatial similarity compares the location of a newly-detected object and the predicted location of tracked tool in the current video frame. The tool ID match metric simply compares the tool ID of the newly-detected object with the tool ID associated with an existing track. Note that tool tracking module 106 can evaluate the set of metrics for each new detection individually or collectively. In some embodiments, when the set of metrics are evaluated collectively, tool tracking module 106 can use a lost function that combines the set of metrics using a set of weighted loss terms. We now describe each of the set of assignment metrics in more detail.

Note that the semantic similarity metric is applied by tool tracking module 106 to evaluate whether a newly-detected object from a newly processed image is sufficiently similar in appearances to a tracked tool associated with an established track. In some embodiments, to perform the semantic similarity evaluation, the generated bounding box for the new detection is used to crop out a corresponding region of the video frame. The cropped image is then fed into an re-ID model 116 within tool tracking module 106 to generate a feature vector of the predetermined dimension, e.g., 128 dimensions/numbers, or a 128-dimension feature vector. While 128-dimension feature vector (or simply "128 features") may be used to describe the semantic similarity, other embodiments of re-ID model 116 can be trained to generate a feature vector of other predetermined dimensions, e.g., 64 or 256 without departing from the scope of the present techniques. Because the features/numbers in a given extracted feature vector encode the image features such as shapes, textures of the cropped image, they can be referred to as "semantic features" and the process of generating these feature vectors can be referred to as "semantic features embedding." Because the generated bounding boxes by tool detection module 104 can have different dimensions, in some embodiments, tool tracking module 106 is configured to resize each received cropped image into a common input image size before passing it though re-ID model 116.

For semantic similarity evaluation, we assume at least one track has been initialized or instantiated. Because each established track is constructed from a sequence of previously detected and cropped images of the tool, a set of semantic feature vectors associated with the set of previous detections of the tool has been extracted and become part of the established track, and stored in a memory. In various embodiments, each established track can have the following attributes: (1) an array of semantic feature vectors corresponding to a set of previous detections of the tracked tool; and (2) an array of the predicted location of the tracked tool corresponding to the set of previous detections of the tracked tool. In an initial frame, the semantic feature array is initialized through the semantic features embedding by re-ID model 116, and the center of assigned bounding box is used for initial track location prediction. In some embodiments, each established track can have the following mathematical expression: {pred or 'P': [($x_0$, $y_0$), ($x_1$, $y_1$), ($x_2$, $y_2$), . . . ]; 'semantic feature' or 'F': [$f_0$, $f_1$, $f_2$, . . . ]}, wherein 'P' is the array of the predicted locations and 'F' is the array of the semantic feature vectors. Note that the two arrays have one-to-one correspondences. Moreover, the two arrays of the established track also both correspond to a same timing array 'T': [$t_0$, $t_1$, $t_2$, . . . ] of a set of detection timestamps for the set of previous detections.

Hence, the newly computed semantic feature vector of a newly-detected object can be compared with these historic semantic feature vectors associated with each established track to determine whether the newly-detected object and the previously detected images of the tool are visually similar. In other words, to determine if the newly-detected object belongs to one of the established tracks (e.g., a left-tool track and a right-tool track), a feature-vector-based comparison is made to between the newly-computed feature vector and the stored semantic feature vectors associated with the established track, referred to as the "the semantic similarity metric." Note that the semantic similarity metric or the semantic similarity comparison is one of the key decision-making mechanisms in the proposed multi-tool tracking system. It can be quite effective in such scenarios when multiple objection detections are made in the middle of a given frame so that the spatial similarity metric cannot reliably assign the multiple detentions to the corresponding tracks. Moreover, the semantic similarity metric plays a highly important role in the tool re-ID portion of the multi-tool tracking system. For example, after a tool has been moved temporally out of the camera viewpoint, and when the tool re-enters the screen, the semantic similarity metric is used to ensure that the new detection of the tool belongs to the established track of the same tool.

In some embodiments, a Euclidean distance can be computed between the newly-computed feature vector and the historic feature vectors associated with the established track. In a particular embodiments, given a detection d, at a timestamp t and an existing track k, we also denote fa as the extracted semantic feature vector from the corresponding bounding box. It is also assumed that the existing track k is associated with an array F of extracted feature vectors of the detected tool from a timestamp 0 to a timestamp t–1, wherein $F=[f_0, f_1, . . . , f_{t-1}]$. Euclidean distance between fa and each of the feature detectors in array F is first calculated. The set of computed distances/similarities is sorted in an increasing order. Next, the average of a predetermined portion (e.g., 10%) of the similarity data is used as the semantic distance/similarity between the track/and detection d.

In some embodiments, the computed semantic distance/similarity is further compared with a predetermined similarity threshold. If the computed semantic distance/similarity is greater than the semantic similarity threshold, it is a strong indicator that the newly-detected object does not belong to the given track. However, if the computed semantic distance/similarity is smaller than the semantic similarity threshold, it may not be sufficient to assign the newly-detected object to the given track. For example, it is possible that both tracked tools are of the same type so that they have very similar appearances (and therefore the small difference in semantic similarity). Hence, it is necessary to also look at the spatial similarity between the location of the detected tool and the given track.

In some embodiments, when computing the semantic similarity between the newly-detected object and the established track, tool tracking module 106 is configured to compare the newly-detected object with the previously-detected tool associated with the track in the last N processed frames immediately before the current frame, instead of just comparing with the last frame immediately before the current frame, wherein N is an integer number. In some embodiments, N corresponds to between 1 to 10 seconds of the processed and stored frame information, e.g., N can be around 100 at a video frame rate of 25-30 fps. As a result, the last N processed frames may be referred to as the short-term memory. One reason that tool tracking module 106 takes into account the short-term memory instead of only the last frame is that an actively tracked tool can have occlusion from tissues, other tools, and other artifacts. As such, only comparing with the last frame or even the last few frames in a given track runs the risk of encountering a fully or partially occlude tool which leads to the loss of tracking accuracy. Moreover, in the case when both the left tool and right tool are of the same type, e.g., graspers, it becomes more challenging for the model to distinguish between these two tools when the semantic similarity comparison is only made with the last frame of the given track. However, when the semantic similarity comparison includes a longer history of the processed frames, detection accuracy can be significantly improved.

Note that a detection gap can exist in an active track when the tracked tool is temporarily out of the view and "lost" from the frames, e.g., due to one of the above-described occlusions, thereby does not generate meaningful historic data for comparison (i.e., no bounding boxes are generated). Such detection gaps can be as long as a few seconds of the video. In some embodiments, the semantic similarity comparisons are made with the short-term memory while avoiding such detection gaps. To do so, each detection gap longer than a predetermined time interval (e.g., longer than 1 second) is tracked and recorded as a part of the established track. Hence, when making semantic similarity comparisons with the short-term memory, tool tracking module 106 can identify such a gap immediately before the current frame. If such a gap exists, tool tracking module 106 can trace back to a time stamp right before the gap, and start making semantic similarity comparisons with N previously fames before the detection gap when the tool has been positively detected. In other words, in these embodiments, the semantic similarity comparisons are made with the latest N frames when actual detections of the tracked tool are made (which characterized with the cropped images and generated bounding boxes).

Returning to the functions of tool tracking module 106, in some embodiments, assigning a newly-detected object to one of multiple established tracks requires combining the semantic similarity metric and the spatial similarity metric. When considered separately, the spatial similarity metric is used to determine whether the location of the newly-detected object matches the latest predicted location of a tracked tool in an established track. From a tool track perspective, the spatial similarity metric is used to ensure that the new detection is sufficiently close to the latest predicted location of the corresponding track. For example, if an established track is tracking the right-hand tool, the new detection of the same tool will most-likely appear on the right side of the frame. When there are multiple established tracks, the spatial similarity metric is applied to each of the established tracks. For example, when there is a left-tool track and a right-tool track, a first newly-detected object located on the left side of the video image is more likely associated with the left-tool track, whereas another newly-detected object located on the right side of the video image is more likely associated with the right-tool track. In other words, it is assumed that there is no significant jump from the location of a given tool in the immediate proceeding frame to the current frame.

In some embodiments, tool tracking module 106 may apply a predetermine spatial-distance threshold to the spatial similarity metric to determine if the location of a newly-detected object is sufficient similar/close to a given predicted location of an established track. In some embodiments, if the spatial distance between the location of a new detection and any of the latest predicted locations of the established tracks is greater than the predetermine spatial-distance threshold, a very large weight will be given to the potential assignment of an edge connecting the new detection and any of such predicted locations.

Note that the location of the detected tool is already known from the associated bounding box. For example, tool tracking module 106 can use the center of the generated bounding box as the location of the detected tool. In some embodiments, tool tracking module 106 may use the center of the right edge of the generated bounding box the location of the location of the detected tool. Separately, tool tracking module 106 may use a Kalman filter configured to predict the new position of a tracked tool in the current frame. Note that the size of the bounding box of a tracked tool tends to change from frame to frame due to a number of dynamic factors, such as perspective changes of the tool due to tool movement, change in the perspective of the camera, change in jaw actions (i.e., open jaw vs. closed jaw), and a combination of the above. As a result, it has been found that using the center of the bounding box as the location of the detected tool over using an edge point of the bounding box can achieve better tracking performances. Hence, the center of the bounding box of a newly-detected object can be used to compare with the predicted location of a tracked tool in the corresponding track.

In some embodiments, to simultaneously track multiple tools through a sequence of video frames based on multiple established tracks (e.g., a left and a right-tool tracks) under multiple assignment metrics (including the semantic similarity metric and the spatial similarity metric), tool tracking module 106 uses a data association technique to attempt to assign each detected tool within a new frame to an established track in the multiple established tracks. In some embodiments, the data association technique includes a Hungarian method which is configured to assign the detected tools to their corresponding tracks. In some embodiments, the objective of the proposed Hungarian method is to minimize the total cost for all of the detections rather than minimizing element wise cost (i.e., for each detection). In these embodiments, a total cost function for all of the detections and all of the established tracks is constructed and minimized. For example, if there are 3 detected objects in the current frame, and 3 existing tracks, a single cost function will be constructed for the 3 detected objects and 3 existing tracks, so that the proposed Hungarian method will attempt to simultaneously assign each of the 3 detected objects to a right track in the 3 existing tracks by minimizing the single cost function.

Mathematically, to be able to associate detected objects with the tracks, a cost matrix between each active track/and each new detection d may be first constructed. Next, the cost matrix is minimized using the Hungarian algorithm. The cost function is defined in Eqn. 1, which is a combination of (1) semantic similarity metric, (2) the spatial-distance similarity metric, and (3) detection ID and track ID matching.

$$\mathrm{cost}(t,d) = D_{fear}(t,d) + M.\ \mathbb{1}_{D_{spatial}(t,d) > \lambda_{sp}} +$$
$$M.\ \mathbb{1}_{d.DetClass \neq t.classID} \tag{1}$$

wherein/denotes a track, d denotes a detection. In Eqn. 1, the first term on the right hand side $D_{fear}(\bullet, \bullet)$ represents the semantic dissimilarity between image feature associated with track/and image features of detection d. As described above, to achieve a real-time performance and adapt to the appearance changes of a track across a sequence of frames, a short-term memory is considered wherein a predetermined number of N recent frames of the given track are used to compare the feature distance to a new detection d in the semantic feature embedding space. The second term in Eqn. 1 represents the spatial distance between the center of detection d and the latest predicted location of the track/(e.g., by using a Kalman filtering technique). Here an assumption is made that surgical tools only move slightly between consecutively frames, which is a reasonably safe assumption under a sufficiently high frame rates, e.g., 25-30 fps. The expression in the second term also indicates that, if the spatial distance is greater than a predetermined distance threshold Asp, then the corresponding element in the cost matrix is given a very high weight to prohibit such an assignment from happening. The third term in Eqn. 1 factors in between the class label of the track (or "track ID") and the class label of the detected tool (or "tool ID"), and hence may be referred to as the "class ID" match term. In the particular expression, the third term in Eqn. 1 adds a very high bias, e.g., M=1000 to the total cost if the class label of the detection does not match the class label of the given track, thereby prohibiting such an assignment from happening.

To solve the cost function of Eqn. 1 using the Hungarian method, a bipartite graph can be constructed wherein the nodes of the bipartite graph are the new detections and the latest predictions for the existing tracks. In this graph, there is an edge connection each new detection and each existing track. Each edge of the graph is also assigned a weight calculated based on the computed semantic similarity and spatial similarity metrics between the new detection and the existing track. After constructing the bipartite graph based on the new detections, the latest predictions for the existing tracks, and the computed semantic similarity and spatial similarity metrics, a bipartite matching is performed to generate the accurate assignments of the new detections in the newly processed frame to the corresponding tracks.

Further referring to MSTT system 100 of FIG. 1, note that tool tracking module 106 is followed by tool re-identification module 108 configure for track recovery, i.e., attempting to assign a new detection to an inactive track. In some embodiments, tool re-identification module 108 receives any new detection that cannot be assigned to any active track at the end of the data association operations by tool tracking module 106, referred to as the unassigned detections 126. Re-identification module 108 is configured to determine whether a received unassigned detection is associated with a tool that was previously tracked in an established track but becomes occluded or moves out of the screen (which also causes the associated established track to become an inactive track). If so, re-identification module 108 attempts to recover such a previously-established track that has been inactive. In some embodiments, re-identification module 108 can use a modified cost function based on Eqn. (1) to assign an unassigned detection d to any inactive track/which is expressed below.

$$\text{cost}(t,d)=D_{fear}(t,d).$$
$$M.\, \mathbb{1}_{D_{spatial(t,d)}\geq \lambda_{sp}/\wedge d.DetClass=t.classID} \tag{2}$$

Note that one modified cost function Eqn. (2) can be constructed between each unassigned detection d to each inactive track t. The intuition behind the modified cost function Eqn. (2) is that, if a tool emerges from an occluded organ, the detection module 102 usually fails to correctly identify the tool as the "missing" tool and therefore would also fail to assign the original tool ID associated with the missing tool. However, it is reasonable to assume that the location of the new detection of the missing tool within the frame is close to the last known location of the inactive track. Consequently, a small spatial distance computed from the last known location can be reliably used to re-assign the unassigned detection to the inactive track. Generally speaking, modified cost function Eqn. (2) to assign a new detection to any inactive track is stricter than cost function Eqn. (1) to assign a new detection to an active track. This is achieved by generating a very high cost value (which naturally prohibits an assignment) if the new detection class ID does not match or the class ID of an inactive track, or if the new detection and the last known location of an inactive track are spatially far apart from each other. However, if the new detection can pass both of the above two similar tests, then a reassignment of the new detection to the inactive track can be made.

Figure 2A:
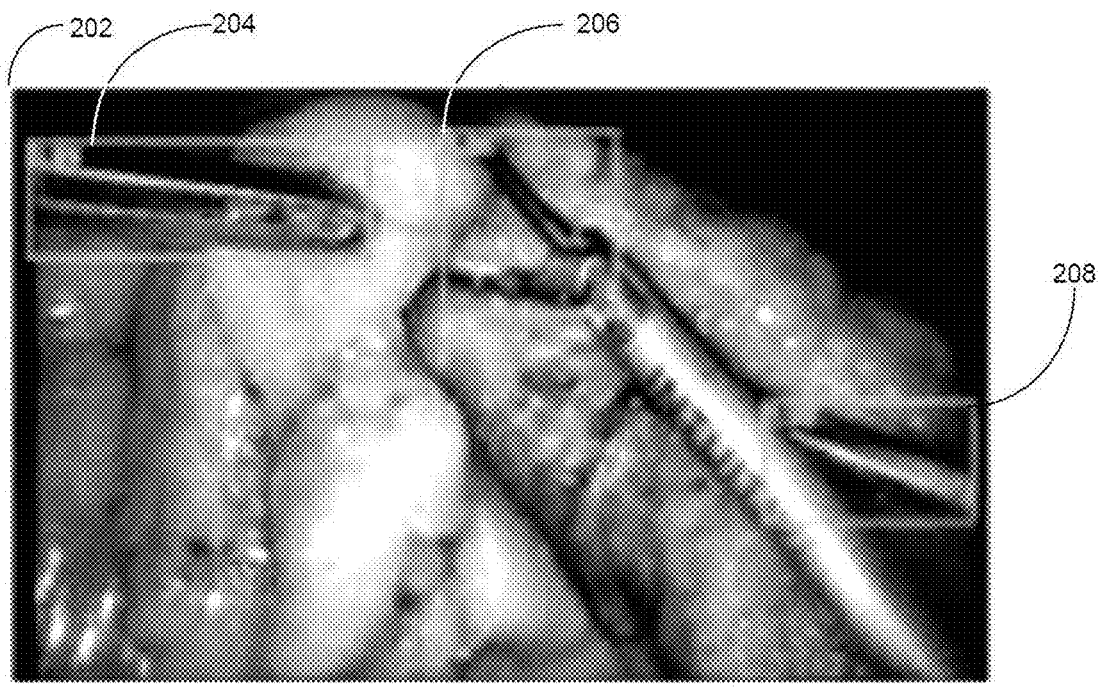
FIG. 2A shows an exemplary processed current frame by the disclosed tool detection module that includes three newly detected objects in accordance with some embodiments described herein.
Figure 2B:
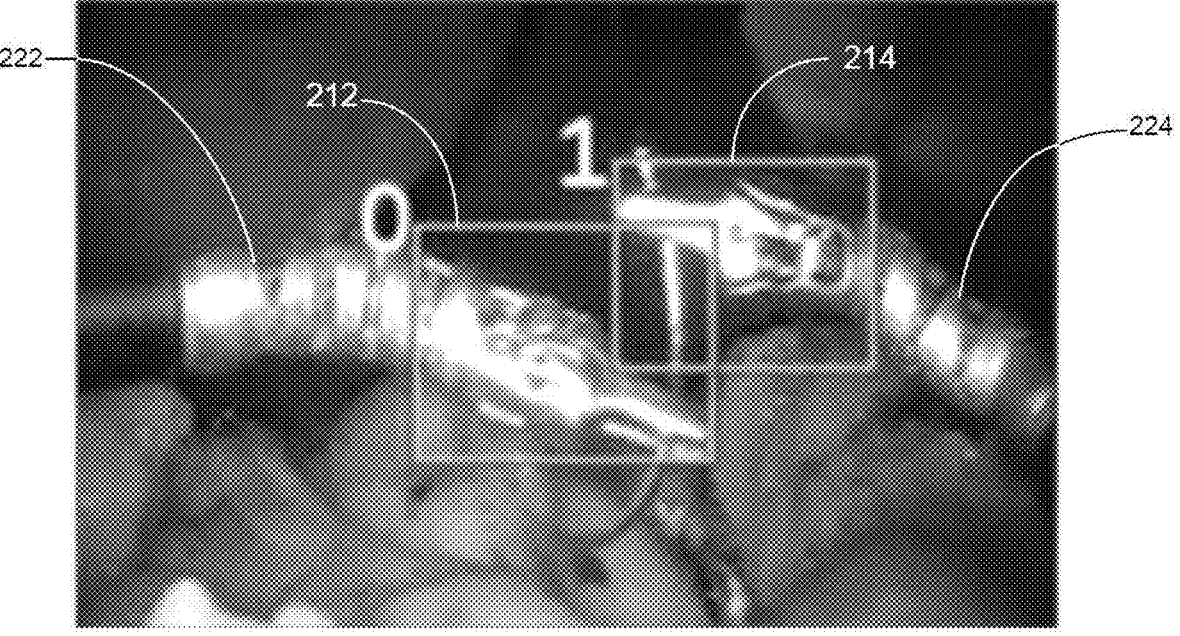
FIG. 2B shows exemplary outputs of the disclosed tool track module after assigning two newly-detected objects to the corresponding left tool and right tool at a given timestamp in accordance with some embodiments described herein.

FIG. 2A shows an exemplary processed current frame 202 by tool detection module 104 that includes three newly detected objects in accordance with some embodiments described herein. As can be seen in FIG. 2A, processed frame 202 includes three generated bounding box 204, 206, and 208 framing the end effectors parts of three detected surgical tool objects. FIG. 2B shows exemplary outputs of tool track module 106 after assigning two newly-detected objects 212 and 214 to the corresponding left tool 222 and right tool 224 at a given timestamp in accordance with some embodiments described herein. As can be seen in FIG. 2B, the first detected object/bounding box 212 is successfully assigned to left tool 212, and the second detected object/bounding box 214 is successfully assigned to right tool 224.

Figure 3:
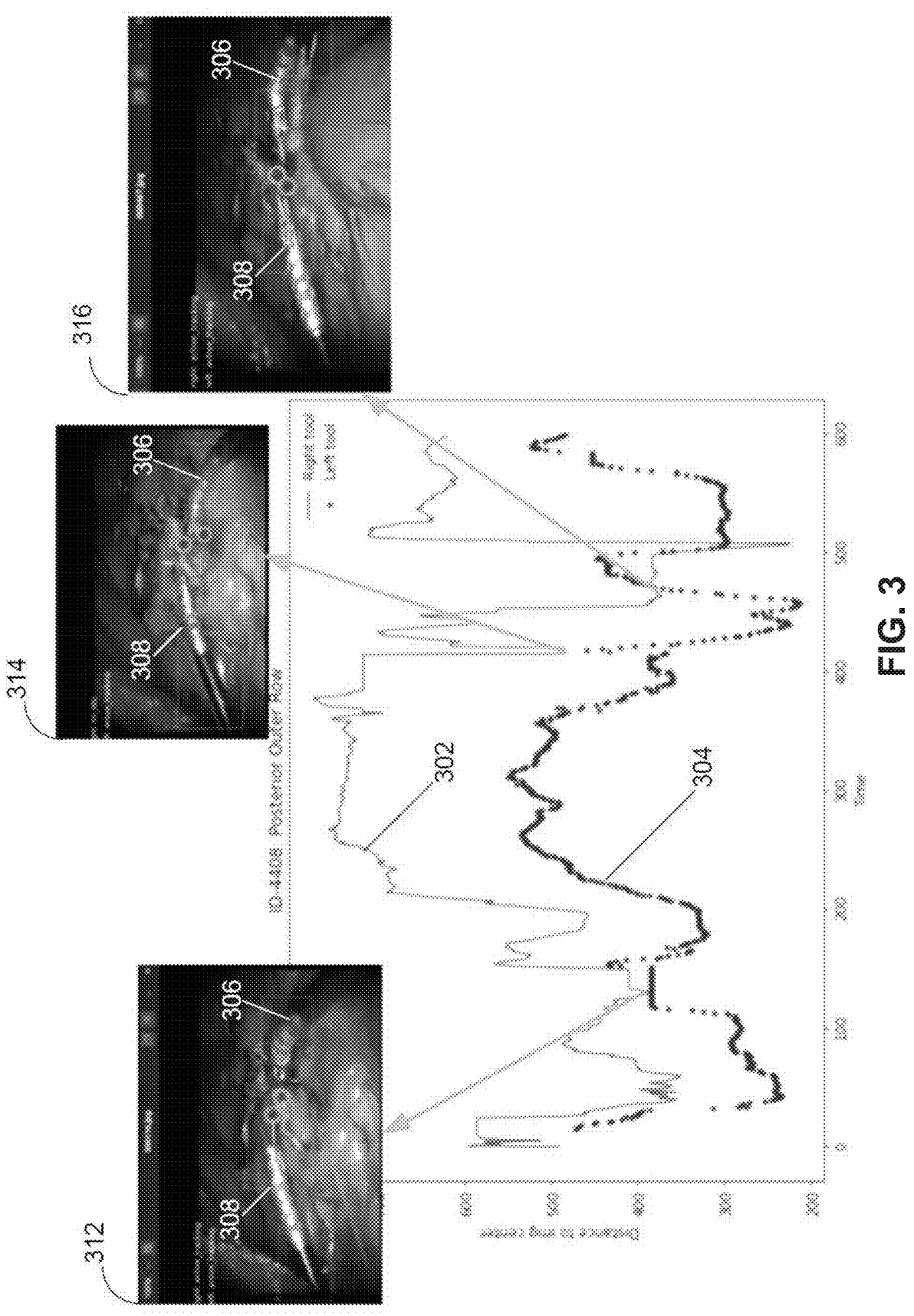
FIG. 3 shows two exemplary established tracks generated by the disclosed MSTT system that tracks a right-hand tool and a left-hand tool in accordance with some embodiments described herein

FIG. 3 shows two exemplary established tracks 302 and 304 generated by the disclosed MSTT system 100 that tracks a right-hand tool 306 and a left-hand tool 308 in accordance with some embodiments described herein. As can be seen in FIG. 3, track 302 is constructed for the right-hand tool 306, whereas track 304 is constructed for the left hand tool 308. FIG. 3 also shows that the disclosed MSTT system 100 is capable of correctly distinguishing the left-hand tool and the right-hand tool at three instances when the two tools are extremely close to each other and assigning the two new detections in each of the instances to the right track. Note that the exemplary tracking process of FIG. 3 also demonstrates that the disclosed MSTT system 100 is capable of tracking the multiple tools for an extended time period, e.g., >10 minutes in this example.

FIG. 4 presents a flowchart illustrating an exemplary process 400 for tracking one or more surgical tools through a sequence of video frames of a surgical video in accordance with some embodiments described herein. In one or more embodiments, one or more of the steps in FIG. 4 may be omitted, repeated, and/or performed in a different order. Accordingly, the specific arrangement of steps shown in FIG. 4 should not be construed as limiting the scope of the technique.

Process 400 may begin by receiving one or more established tracks for one or more previously-detected surgical tools (step 402). In some embodiments, the one or more previously-detected surgical tools are detected by a Faster-RCNN model trained to localized and classify a set of diverse types of surgical tools within a given video frame of a surgical video. In some embodiments, the Faster-RCNN detection model is trained to simultaneously detect and classify two surgical tools of the same type (e.g., a left-hand grasper and a right-hand grasper) within a given video frame.

Process 400 subsequently receives a current frame within a sequence of video frames (step 404) and processes the current frame to detect one or more objects using the same deep-learning model (step 406). Next, process 400 next computes a semantic similarity metric between each of the detected one or more objects and each of the established tracks (step 408). In some embodiments, process 400 computes the semantic similarity metric by first extracting a set of image features from the detected one or more objects using a re-identification (re-ID) model. Process 400 then computes the semantic similarity metric by comparing the set of extracted image features with multiple sets of historic image features associated with the established track to determine whether the newly-detected object and the detected tool associated with the established tracks are visually similar to each other. In some embodiments, the set of image features forms a feature vector with 128 dimensions.

Process 400 additionally computes a spatial similarity metric between each of the detected one or more objects and the latest predicted location for each of the established tracks (step 410). In some embodiments, prior to computing the spatial similarity metric, process 400 first receives a center location on the generated bounding box for the detected object. Process 400 further computes the latest predicted location for the established track by applying a Kalman filter to the received center location of the detected object and the last known location of the established track. Subsequently, process 400 attempts to assign each of the detected one or more objects to one of the one or more established tracks based on the computed semantic similarity metric and the spatial similarity metric for the detected object, the tool ID for the established track and the tool ID for the detected object (step 412). In some embodiments, to assign a given detected object to one of the established tracks, process 400 uses a data association technique on the computed semantic similarity metrics and the spatial similarity metrics between the given detected object and the one or more established tracks. Specifically, the data association technique employs a Hungarian method that is configured to identify a correct track assignment of the detected object by minimizing a cost function of the assignment between the given detected object and the one or more established tracks. In some embodiments, process 400 a bipartite graph to solve the cost function associated with each detected object.

Figure 5:
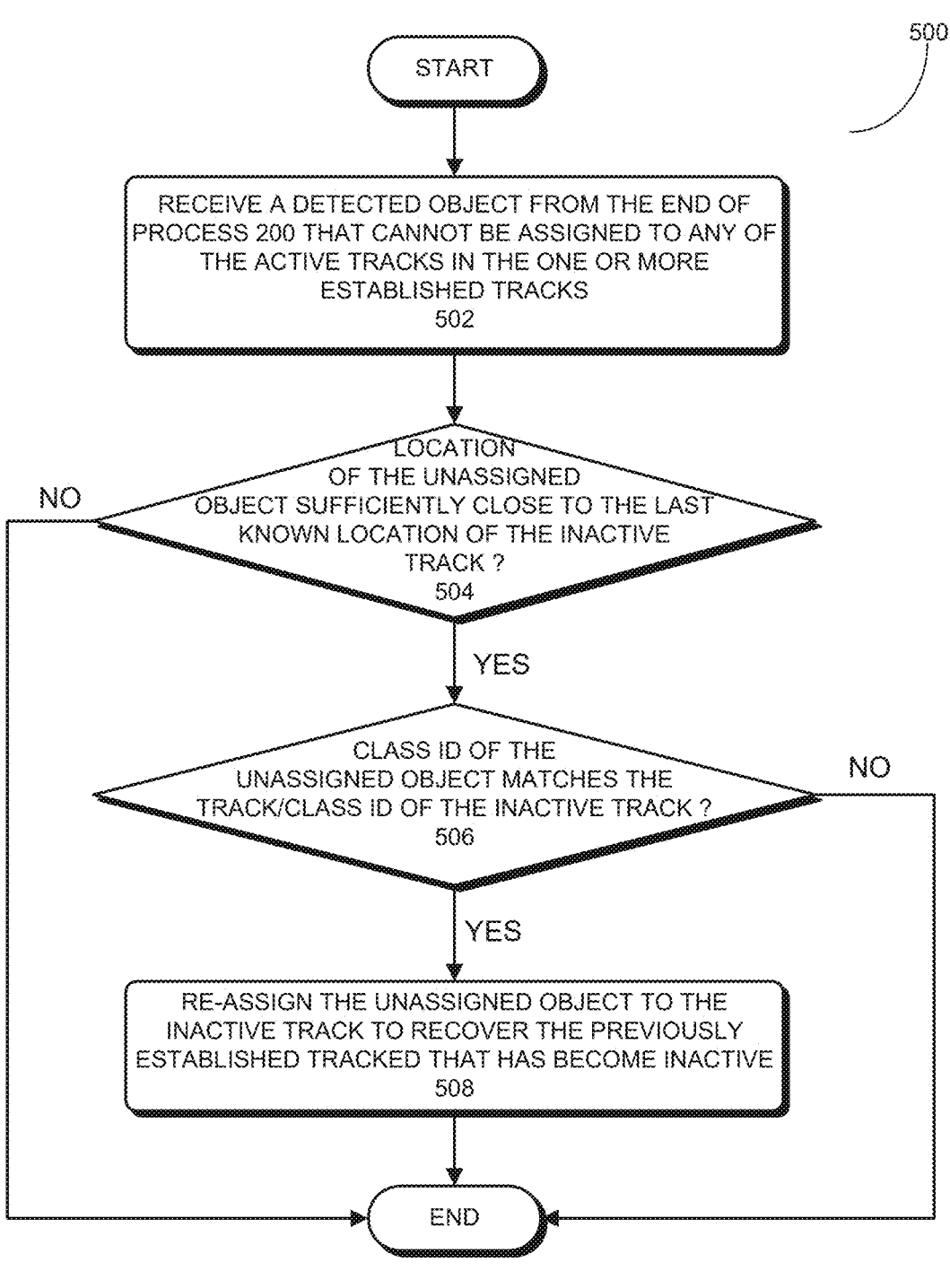
FIG. 5 presents a flowchart illustrating an exemplary process for attempting to recovery an inactive track previously established in accordance with some embodiments described herein.

FIG. 5 presents a flowchart illustrating an exemplary process 500 for attempting to recovery an inactive track previously established in accordance with some embodiments described herein. In one or more embodiments, one or more of the steps in FIG. 5 may be omitted, repeated, and/or performed in a different order. Accordingly, the specific arrangement of steps shown in FIG. 5 should not be construed as limiting the scope of the technique.

Process 500 may begin by receiving a detected object from the end of process 400 that cannot be assigned to any of the active tracks in the one or more established tracks (step 502). Note that an established track can become an inactive track when the associated surgical tool is temporarily occluded by an organ or temporarily moves out of the video frames. Next, process 500 determines if the location of the unassigned object is sufficiently close to the last known location of the inactive track (step 504). If not, process 500 terminates. However, if the location of the unassigned object is sufficiently close to the last known location of the inactive track, process further determines if the class ID associated with the unassigned object matches the track/tool ID of the inactive track (step 506). If not, process 500 terminates. However, if the class ID of the unassigned object matches the track/tool ID of the inactive track, process 500 re-assigns the unassigned object to the inactive track to recover the previously established tracked that has become inactive (step 508).

Figure 6:
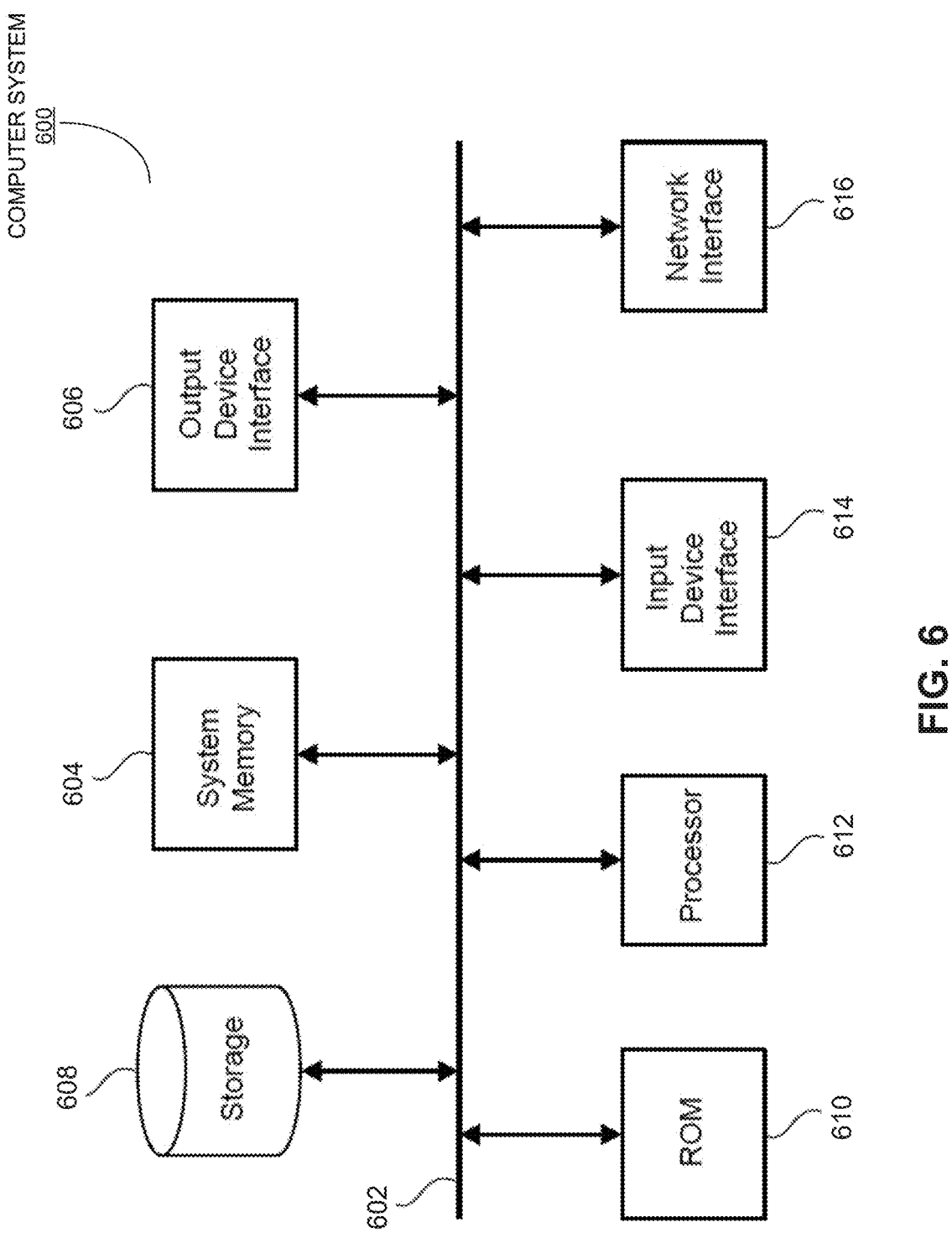
FIG. 6 conceptually illustrates a computer system with which some embodiments of the subject technology can be implemented.

FIG. 6 conceptually illustrates a computer system with which some embodiments of the subject technology can be implemented. Computer system 600 can be a client, a server, a computer, a smartphone, a PDA, a laptop, or a tablet computer with one or more processors embedded therein or coupled thereto, or any other sort of computing device. Such a computer system includes various types of computer-readable media and interfaces for various other types of computer-readable media. Computer system 600 includes a bus 602, processing unit(s) 612, a system memory 604, a read-only memory (ROM) 610, a permanent storage device 608, an input device interface 614, an output device interface 606, and a network interface 616. In some embodiments, computer system 600 is a part of a robotic surgical system.

Bus 602 collectively represents all system, peripheral, and chipset buses that communicatively connect the numerous internal devices of computer system 600. For instance, bus 602 communicatively connects processing unit(s) 612 with ROM 610, system memory 604, and permanent storage device 608.

From these various memory units, processing unit(s) 612 retrieves instructions to execute and data to process in order to execute various processes described in this patent disclosure, including the above-described multiple surgical tool detection and tracking techniques described in conjunction with FIGS. 1-5. The processing unit(s) 612 can include any type of processor, including, but not limited to, a microprocessor, a graphic processing unit (GPU), a tensor processing unit (TPU), an intelligent processor unit (IPU), a digital signal processor (DSP), a field-programmable gate array (FPGA), and an application-specific integrated circuit (ASIC). Processing unit(s) 612 can be a single processor or a multi-core processor in different implementations.

ROM 610 stores static data and instructions that are needed by processing unit(s) 612 and other modules of the computer system. Permanent storage device 608, on the other hand, is a read-and-write memory device. This device is a non-volatile memory unit that stores instructions and data even when computer system 600 is off. Some implementations of the subject disclosure use a mass-storage device (such as a magnetic or optical disk and its corresponding disk drive) as permanent storage device 608.

Other implementations use a removable storage device (such as a floppy disk, flash drive, and its corresponding disk drive) as permanent storage device 608. Like permanent storage device 608, system memory 604 is a read-and-write memory device. However, unlike storage device 608, system memory 604 is a volatile read-and-write memory, such as a random access memory. System memory 604 stores some of the instructions and data that the processor needs at runtime. In some implementations, various processes described in this patent disclosure, including the above-described multiple surgical tool detection and tracking techniques described in conjunction with FIGS. 1-5, are stored in system memory 604, permanent storage device 608, and/or ROM 610. From these various memory units, processing unit(s) 612 retrieves instructions to execute and data to process in order to execute the processes of some implementations.

Bus 602 also connects to input and output device interfaces 614 and 606. Input device interface 614 enables the user to communicate information to and select commands for the computer system. Input devices used with input device interface 614 include, for example, alphanumeric keyboards and pointing devices (also called "cursor control devices"). Output device interface 606 enables, for example, the display of images generated by the computer system 600. Output devices used with output device interface 606 include, for example, printers and display devices, such as cathode ray tubes (CRT) or liquid crystal displays (LCD). Some implementations include devices such as a touchscreen that functions as both input and output devices.

Finally, as shown in FIG. 6, bus 602 also couples computer system 600 to a network (not shown) through a network interface 616. In this manner, the computer can be a part of a network of computers (such as a local area network ("LAN"), a wide area network ("WAN"), an intranet, or a network of networks, such as the Internet. Any or all components of computer system 600 can be used in conjunction with the subject disclosure.

The various illustrative logical blocks, modules, circuits, and algorithm steps described in connection with the embodiments disclosed in this patent disclosure may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The hardware used to implement the various illustrative logics, logical blocks, modules, and circuits described in connection with the aspects disclosed herein may be implemented or performed with a general purpose processor, a digital signal processor (DSP), an application-specific integrated circuit (ASIC), a field-programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of receiver devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored as one or more instructions or code on a non-transitory computer-readable storage medium or non-transitory processor-readable storage medium. The steps of a method or algorithm disclosed herein may be embodied in processor-executable instructions that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include RAM, ROM, EEPROM, flash memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer-program product.

While this patent document contains many specifics, these should not be construed as limitations on the scope of any disclosed technology or of what may be claimed, but rather as descriptions of features that may be specific to particular embodiments of particular techniques. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described, and other implementations, enhancements and variations can be made based on what is described and illustrated in this patent document.

What is claimed is:

1. A computer-implemented method for tracking surgical tools in a surgical video, the method comprising:

receiving a current video frame of the surgical video for processing;

receiving one or more established tracks for one or more previously-detected surgical tools in the surgical video, wherein each established track comprises a first array that has a plurality of previously-predicted locations of a previously-detected surgical tool and a second array of semantic features associated with the previously-detected surgical tool across a plurality of previously-processed video frames of the surgical video;

processing the current video frame of the surgical video to detect one or more objects using a first deep-learning model; and for each detected object in the one or more detected objects, computing a semantic similarity metric between the detected object and each of the one or more established tracks by:

using a second deep-learning model to extract a set of semantic features of the detected object;

determining whether an established track comprises a detection gap in which a corresponding previously-detected surgical tool is temporarily out of view from a first subset of previously-processed video frames of the plurality of previously-processed video frames immediately before to the current video frame over a predefined time interval; and responsive to the established track comprising the detection gap, comparing the set of semantic features with one or more semantic features of the second array across a second subset of previously-processed video frames of the plurality of previously-processed video frames immediately before to the first subset of previously-processed video frames to determine whether the detected object and the corresponding previously-detected surgical tool are visually similar;

computing a spatial similarity metric between the detected object and a latest predicted location in the first array for each of the one or more established tracks; and assigning the detected object to one of the one or more established tracks based on the computed semantic similarity metric and the computed spatial similarity metric.

2. The computer-implemented method of claim 1, wherein prior to processing the current video frame, the method further comprises:

converting a frame rate of the surgical video so that the converted frame rate is greater or equal to a predetermined frame rate; and resizing the current video frame into a predetermined image size.

3. The computer-implemented method of claim 1, wherein the first deep-learning model is a Faster-RCNN model trained to detect and classify a set of diverse types of surgical tools within a given video frame of the surgical video.

4. The computer-implemented method of claim 1, wherein the one or more previously-detected surgical tools include a left-hand tool and a right-hand tool.

5. The computer-implemented method of claim 1, wherein the set of semantic features forms a feature vector of 128 dimensions.

6. The computer-implemented method of claim 1, wherein the second array of semantic features are associated with a number of previously-detected images of the surgical tool over a predetermined time period.

7. The computer-implemented method of claim 1, wherein prior to computing the spatial similarity metric, the method further comprises:

receiving a location on a generated bounding box for the detected object; and generating the latest predicted location for the established track by applying a Kalman filter to the received location of the detected object and a last known location of the established track within the first array.

8. The computer-implemented method of claim 7, wherein the location of the generated bounding box is a center of the generated bounding box.

9. The computer-implemented method of claim 1, wherein assigning the detected object to one of the one or more established tracks includes using a data association technique on the computed semantic similarity metric and the computed spatial similarity metric between the detected object and each of the one or more established tracks.

10. The computer-implemented method of claim 9, wherein the data association technique employs a Hungarian method that is configured to identify a correct track assignment within the one or more established tracks for the detected object by minimizing a cost function of a track assignment between the detected object and the one or more established tracks.

11. The computer-implemented method of claim 10, wherein the Hungarian method employs a bipartite graph to solve the cost function associated with the detected object.

12. The computer-implemented method of claim 10, wherein the method further comprises assigning a weight greater than a threshold to the track assignment if a corresponding computed spatial similarity metric is greater than a predetermined distance threshold to prohibit the track assignment.

13. The computer-implemented method of claim 10, wherein the cost function additionally includes a track ID associated with the established track and a class ID assigned to the detected object.

14. The computer-implemented method of claim 13, wherein the method further comprises assigning a weight greater than a threshold to the track assignment if a corresponding track ID associated with the established track does not match the class ID of the detected object to prohibit the track assignment.

15. The computer-implemented method of claim 1, wherein the method further comprises:

responsive to a determination that a previously detected object is undetectable, identify one of the one or more established tracks as an inactive established track;

after the previously detected object has been undetectable for a plurality of video frames of the surgical video, receiving an unassigned object in the one or more detected objects that cannot be assigned to any track in the one or more established tracks;

determining if a location of the unassigned object is sufficiently close to a last known location of the inactive established track in the one or more established tracks and if a class ID of the unassigned object matches a track ID of the inactive established track; and if so, re-assigning the unassigned object to the inactive established track to reactivate the inactive established track.

16. The computer-implemented method of claim 1, wherein, responsive to the established track not including the detection gap, comparing the set of semantic features with the one or more semantic features of the second array across a third subset of previously-processed video frames of the plurality of previously-processed video frames immediately before the current video frame.

17. An apparatus, comprising:

one or more processors; and a memory coupled to the one or more processors, wherein the memory stores instructions that, when executed by the one or more processors, cause the apparatus to:

receive a current video frame of a surgical video for processing;

receive one or more established tracks for one or more previously-detected surgical tools in the surgical video, wherein each established track comprises a first array that has a plurality of previously-predicted locations of a previously-detected surgical tool and a second array of semantic features associated with the previously-detected surgical tool across a plurality of previously-processed video frames of the surgical video;

process the current video frame of the surgical video to detect one or more objects using a first deep-learning model; and for each detected object in the one or more detected objects, compute a semantic similarity metric between the detected object and each of the one or more established tracks by:

using a second deep-learning model to extract a set of semantic features of the detected object;

determining whether an established track comprises a detection gap in which a corresponding previously-detected surgical tool is temporarily out of view from a first subset of previously-processed video frames of the plurality of previously-processed video frames immediately before to the current video frame over a predefined time interval; and responsive to the established track comprising the detection gap, comparing the set of semantic features with one or more semantic features of the second array across a second subset of previously-processed video frames of the plurality of previously-processed video frames immediately before to the first subset of previously-processed video frames to determine whether the detected object and the corresponding previously-detected surgical tool are visually similar;

compute a spatial similarity metric between the detected object and a latest predicted location in the first array for each of the one or more established tracks; and assign the detected object to one of the one or more established tracks based on the computed semantic similarity metric and the computed spatial similarity metric.

18. The apparatus of claim 17, wherein the memory coupled to the one or more processors, wherein the memory stores instructions that, when executed by the one or more processors, cause the apparatus to:

responsive to a determination that a previously detected object is undetectable, identifying one of the one or more established tracks as an inactive established track;

after the previously detected object has been undetectable for a plurality of video frames of the surgical video, receive an unassigned object in the one or more detected objects that cannot be assigned to any track in the one or more established tracks;

determine if a location of the unassigned object is sufficiently close to a last known location of an inactive track in the one or more established tracks and if a class ID of the unassigned object matches a track ID of the inactive track; and if so, re-assign the unassigned object to the inactive established track to reactivate the inactive established track.

19. A system, comprising:

one or more processors; and a memory coupled to the one or more processors, wherein the memory stores instructions that, when executed by the one or more processors, cause the system to:

receive a current video frame of a surgical video for processing;

receive one or more established tracks for one or more previously-detected surgical tools in the surgical video, wherein each established track comprises a first array that has a plurality of previously-predicted locations of a previously-detected surgical tool and a second array of semantic features associated with the previously-detected surgical tool across a plurality of previously-processed video frames of the surgical video;

process the current video frame of the surgical video to detect one or more objects using a first deep-learning model; and for each detected object in the one or more detected objects, compute a semantic similarity metric between the detected object and each of the one or more established tracks by:

using a second deep-learning model to extract a set of semantic features of the detected object;

determining whether an established track comprises a detection gap in which a corresponding previously-detected surgical tool is temporarily out of view from a first subset of previously-processed video frames of the plurality of previously-processed video frames immediately before to the current video frame over a predefined time interval; and responsive to the established track comprising the detection gap, comparing the set of semantic features with one or more semantic features of the second array across a second subset of previously-processed video frames of the plurality of previously-processed video frames immediately before to the first subset of previously-processed video frames to determine whether the detected object and the corresponding previously-detected surgical tool are visually similar;

compute a spatial similarity metric between the detected object and a latest predicted location in the first array for each of the one or more established tracks; and assign the detected object to one of the one or more established tracks based on the computed semantic similarity metric and the computed spatial similarity metric.

20. The system of claim 19, wherein the memory coupled to the one or more processors, wherein the memory stores instructions that, when executed by the one or more processors, cause the system to:

responsive to a determination that a previously detected object is undetectable, identify one of the one or more established tracks as an inactive established track;

after the previously detected object has been undetectable for a plurality of video frames of the surgical video, receive an unassigned object in the one or more detected objects that cannot be assigned to any track in the one or more established tracks;

determine if a location of the unassigned object is sufficiently close to a last known location of the inactive established track in the one or more established tracks and if a class ID of the unassigned object matches a track ID of the inactive established track; and if so, re-assign the unassigned object to the inactive established track to reactivate the inactive established track.

* * * * *